(12) United States Patent
Marotta et al.

(10) Patent No.: US 6,695,876 B1
(45) Date of Patent: *Feb. 24, 2004

(54) ENDOVASCULAR PROSTHESIS

(76) Inventors: Thomas R. Marotta, 857 Sauve Ct., North Vancouver, British Columbia (CA), V7K 3C8; Brian Moore, 500 W. Middlefield Rd. #95, Mountain View, CA (US) 94043; Nikki Toyama, 2155 Ashby Ave., Berkeley, CA (US) 94705; Todd Dickson, 151 Surfway #19, Monterey, CA (US) 93940

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/501,982

(22) Filed: Feb. 11, 2000

Related U.S. Application Data

(60) Provisional application No. 60/119,861, filed on Feb. 12, 1999.

(51) Int. Cl.[7] .................................................. A61F 2/06
(52) U.S. Cl. ...................................... 623/1.15; 606/200
(58) Field of Search ........................... 606/1, 108, 194, 606/195, 198, 200; 623/1.1, 1.11, 1.15, 1.16, 1.17, 1.35

(56) References Cited

U.S. PATENT DOCUMENTS

| | | | |
|---|---|---|---|
| 5,593,442 A | | 1/1997 | Klein |
| 5,662,702 A | | 9/1997 | Keranen |
| 5,693,085 A | * | 12/1997 | Buirge et al. ............... 606/192 |
| 5,713,949 A | * | 2/1998 | Jayaraman ................. 606/198 |
| 5,782,906 A | * | 7/1998 | Marshall et al. ............. 623/1.1 |
| 5,861,025 A | | 1/1999 | Boudghene et al. ........... 623/1 |
| 6,068,655 A | * | 5/2000 | Seguin et al. ................ 623/12 |
| 6,099,560 A | * | 8/2000 | Penn et al. ................ 623/1.35 |
| 6,261,305 B1 | * | 7/2001 | Marotta et al. ............. 606/200 |

FOREIGN PATENT DOCUMENTS

| | | | |
|---|---|---|---|
| WO | WO 98/11846 | 3/1998 | ............. A61F/2/04 |
| WO | WO 99/17681 | 4/1999 | ............. A61F/2/06 |
| WO | WO 99/40873 | 8/1999 | ............. A61F/2/06 |
| WO | WO 99/58084 | 11/1999 | ............. A61F/2/06 |

* cited by examiner

Primary Examiner—Michael J. Milano
Assistant Examiner—(Jackie) Tan Uyen T. Ho
(74) Attorney, Agent, or Firm—Katten Muchin Zavis Rosenman

(57) ABSTRACT

An expandable endovascular prosthesis comprising: body having a proximal end and a distal end; a first expandable portion disposed between the proximal end and the distal end, the tubular first expandable portion being expandable from a first, unexpanded state to a second, expanded state with a radially outward force thereon to urge the first expandable portion against a vascular lumen; and a second expandable portion attached to the first tubular expandable portion; the second expandable portion being expandable upon expansion of the tubular first expandable portion. The endovascular prosthesis is particularly useful in the treatment of aneurysms, particularly saccular aneurysms. Thus, the first expandable portion serves the general purpose of fixing the endovascular prosthesis in place at a target vascular lumen or body passageway in the vicinity at which the aneurysm is located and, upon expansion of the first expandable portion, the second expandable portion expands to block the aneurysmal opening thereby leading to obliteration of the aneurysm. A method of delivering and implanting the endovascular prosthesis is also described.

29 Claims, 8 Drawing Sheets

ENDOVASCULAR PROSTHESIS

This application claims the benefit of U.S. Provisional application Ser. No. 60/119,861, filed Feb. 12, 1989.

BACKGROUND OF THE INVENTION

1. Field of the Invention

In one of its aspects, the present invention relates to an endovascular prosthesis. In another of its aspects, the present invention relates to a method of treating an aneurysm in a patient.

2. Brief Description of the Prior Art

As is known in the art, an aneurysm is an abnormal bulging outward in the wall of an artery. In some cases, the bulging may be in the form of a smooth bulge outward in all directions from the artery—this is known as a "fusiform aneurysm". In other cases, the bulging may be in the form of a sac arising from an arterial branching point or from one side of the artery—this is known as a "saccular aneurysm".

While aneurysms can occur in any artery of the body, it is usually those which occur in the brain which lead to the occurrence of a stroke. Most saccular aneurysms which occur in the brain have a neck which extends from the cerebral blood vessel and broadens into a pouch which projects away from the vessel.

The problems caused by such aneurysms can occur in several different ways. For example, if the aneurysm ruptures, blood enters the brain or the subarachnoid space (i.e., the space closely surrounding the brain)—the latter is known as aneurysmal subarachnoid hemorrhage. This followed by one or more of the following symptoms: nausea, vomiting, double vision, neck stiffness and loss of consciousness. Aneurysmal subarachnoid hemorrhage is an emergency medical condition requiring immediate treatment. Indeed, 10–15% of patients with the condition die before reaching the hospital for treatment. More than 50% of patients with the condition will die within the first thirty days after the hemorrhage. Of those patients who survive, approximately half will suffer a permanent stroke. Some of these strokes occur one to two weeks after the hemorrhage itself from vasospasm in cerebral vessels induced by the subarachnoid hemorrhage. Aneurysms also can cause problems which are not related to bleeding although this is less common. For example, an aneurysm can form a blood clot within itself which can break away from the aneurysm and be carried downstream where it has the potential to obstruct an arterial branch causing a stroke. Further, the aneurysm can also press against nerves (this has the potential of resulting in paralysis or abnormal sensation of one eye or of the face) or the adjacent brain (this has the potential of resulting in seizures).

Given the potentially fatal consequences of the aneurysms, particularly brain aneurysms, the art has addressed treatment of aneurysms using various approaches.

Generally, aneurysms may be treated from outside the blood vessels using surgical techniques or from the inside using endovascular techniques (the latter falls under the broad heading of interventional (i.e., non-surgical) techniques).

Surgical techniques usually involve a craniotomy requiring creation of an opening in the skull of the patient through which the surgeon can insert instruments to operate directly on the brain. In one approach, the brain is retracted to expose the vessels from which the aneurysm arises and then the surgeon places a clip across the neck of the aneurysm thereby preventing arterial blood from entering the aneurysm. If there is a clot in the aneurysm, the clip also prevents the clot from entering the artery and obviates the occurrence of a stroke. Upon correct placement of the clip the aneurysm will be obliterated in a matter of minutes. Surgical techniques are the most common treatment for aneurysms. Unfortunately, surgical techniques for treating these conditions are regarded as major surgery involving high risk to the patient and necessitate that the patient have strength even to have a chance to survive the procedure.

As discussed above, endovascular techniques are non-surgical techniques and are typically performed in an angiography suite using a catheter delivery system. Specifically, known endovascular techniques involve using the catheter delivery system to pack the aneurysm with a material which prevents arterial blood from entering the aneurysm—this technique is broadly known as embolization. One example of such an approach is the Guglielmi Detachable Coil which involves intra-aneurysmal occlusion of the aneurysm via a system which utilizes a platinum coil attached to a stainless steel delivery wire and electrolytic detachment. Thus, once the platinum coil has been placed in the aneurysm, it is detached from the stainless steel delivery wire by electrolytic dissolution. Specifically, the patient's blood and the saline infusate act as the conductive solutions. The anode is the stainless steel delivery wire and the cathode is the ground needle which is placed in the patient's groin. Once current is transmitted through the stainless steel delivery wire, electrolytic dissolution will occur in the uninsulated section of the stainless steel detachment zone just proximal to the platinum coil (the platinum coil is of course unaffected by electrolysis). Other approaches involve the use of materials such as cellulose acetate polymer to fill the aneurysm sac. While these endovascular approaches are an advance in the art, they are disadvantageous. Specifically, the risks of these endovascular approaches include rupturing the aneurysm during the procedure or causing a stroke due to distal embolization of the device or clot from the aneurysm. Additionally, concern exists regarding the long term results of endovascular aneurysm obliteration using these techniques. Specifically, there is evidence of intra-aneurysmal rearrangement of the packing material and reappearance of the aneurysm on follow-up angiography.

One particular type of brain aneurysm which has proven to be very difficult to treat, particularly using the surgical clipping or endovascular embolization techniques discussed above occurs at the distal basilar artery. This type of aneurysm is a weak outpouching, usually located at the terminal bifurcation of the basilar artery. Successful treatment of this type of aneurysm is very difficult due, at least in part, to the imperative requirement that all the brainstem perforating vessels be spared during surgical clip placement.

Unfortunately, there are occasions when the size, shape and/or location of an aneurysm make both surgical clipping and endovascular embolization not possible for a particular patient. Generally, the prognosis for such patients is not good.

Accordingly, while the prior art has made advances in the area of treatment of aneurysms, there is still room for improvement, particularly in endovascular embolization since it is such an attractive alternative to major surgery. Specifically, it would be desirable to have an endovascular prosthesis which could be used in the embolization of aneurysms which are difficult or not possible to treat otherwise. It would be further desirable if such an endovascular prosthesis could be used to treat aneurysms currently treated endovascularly while mitigating or obviating the disadvantages associated with current endovascular embolization techniques.

SUMMARY OF THE INVENTION

It is an object of the present invention to provide a novel endovascular prosthesis which obviates or mitigates at least one of the above-mentioned disadvantages of the prior art.

It is another object of the present invention to provide a novel method for endovascular blocking an aneurysmal opening which obviates or mitigates at least one of the above-mentioned disadvantages of the prior art.

Accordingly, in one of its aspects, the present invention relates to an expandable endovascular prosthesis comprising:

a body having a proximal end and a distal end;
 a first expandable portion disposed between the proximal end and the distal end, the first expandable portion being expandable from a first, unexpanded state to a second, expanded state with a radially outward force thereon to urge the first expandable portion against a vascular lumen; and
 a second expandable portion attached to the first expandable portion;
 the second expandable portion being expandable upon expansion of the first expandable portion.

In yet another of its aspects, the present invention relates to a method for endovascular blocking of an aneurysmal opening with a prosthesis comprising: a body having a proximal end and a distal end, a first expandable portion disposed between the proximal end and the distal end, the first expandable portion being expandable from a first, unexpanded state to a second, expanded state with a radially outward force thereon to urge the first expandable portion against a vascular lumen, and a second expandable portion attached to the first expandable portion; the second expandable portion being expandable upon expansion of the first expandable portion, the method comprising the steps of:

disposing the prosthesis on a catheter;
 inserting the prosthesis and catheter within a body passageway by catheterization of the body passageway;
 translating the prosthesis and catheter to a target vascular lumen at which the aneurysm opening is located;
 exerting a radially outward expansive force on the first expandable portion such that the tubular first expandable portion is urged against the target body passageway;
 causing expansion of the first expandable portion to expand the second expandable portion;
 urging the second expandable portion against the aneurysmal opening thereby blocking the aneurysmal opening.

Thus, the present inventors have discovered a novel endovascular prosthesis having the characteristic of a first expandable portion which, when expanded, causes a second expandable portion (connected to the first expandable) to expand. For example, if the first expandable portion is made of a plastically deformable material (e.g., stainless steel), upon expansion, the first expandable portion will plastically deform. Such expansion will expand the second expandable portion. As will be developed hereinbelow, an endovascular prosthesis having these features is desirable, particularly in the treatment of aneurysms.

Preferably, and as will be further developed hereinbelow, the first expandable portion is generally tubular in structure. Indeed, throughout this specification, reference will be made to a first expandable portion which is generally tubular in structure. However, such reference is for illustrative purposes only and those of skill in the art will recognize that it is possible to utilize a non-tubular structure (e.g., a claw-like design which opens upon expansion) as the first expandable portion.

In International Publication Number WO 99/40873 [Marotta et al. (Marotta)], published Aug. 19, 1999, there is taught a novel endovascular approach useful in blocking of an aneurysmal opening, particularly those in saccular aneurysms, leading to obliteration of the aneurysm. The approach is truly endovascular in that, with the endovascular prosthesis taught by Marotta, there is no requirement to pack the aneurysmal sac with a material (e.g., such is used with the Guglielmi Detachable Coil). Rather, the endovascular prosthesis taught by Marotta operates on the basis that it serves to block the opening to the aneurysmal sac thereby obviating the need for packing material. Thus, the endovascular prosthesis taught by Marotta is an important advance in the art since it obviates or mitigates many of the disadvantages of the prior art. The endovascular prosthesis taught by Marotta comprises a leaf portion capable of being urged against the opening of the aneurysm thereby closing the aneurysm. In the endovascular prosthesis taught by Marotta, the leaf portion is attached to, and independently moveable with respect to, a body comprising at least one expandable portion. The expandable portion is expandable from a first, unexpanded state to a second, expanded state with a radially outward force thereon. Thus, the body serves the general purpose of fixing the endovascular prosthesis in place at a target body passageway or vascular lumen in the vicinity at which the aneurysmal opening is located and the leaf portion serves the purpose of sealing the aneurysmal opening thereby leading to obliteration of the aneurysm. Thus, as taught by Marotta, the leaf portion functions and is moveable independently of the body of the endovascular prosthesis.

While the endovascular prosthesis taught by Marotta is a significant advance in the art, there is still room for improvement. Specifically, in the preferred embodiment of the endovascular prosthesis taught by Marotta, once the device is deployed and the leaf portion is properly positioned, the surface area of the leaf portion is delimited by the surface area of the tube from which the leaf portion was cut. While this may not be a problem in most instances, there are occasions where the aneurysmal opening is sufficiently large that there exists a real possibility that the leaf portion will not completely close off the aneurysmal opening. On the other hand, if one attempts to increase the size of the leaf portion by cutting it from a larger diameter tube, the diameter of the prosthesis increases which can make it more difficult to navigate into the correct position and to use with conventional delivery devices.

Thus, the present inventors have discovered a novel approach which allows for designing the body of the prosthesis to have a conventional tube diameter while having an expandable portion which expands in response to expansion of the body. Thus, in the present endovascular prosthesis, the body has a proximal end and distal end. Disposed between the proximal end and the distal end, there are at least two expandable portions connected to one another. The first expandable portion is expandable from a first, unexpanded state to a second, expanded state with a radially outward force thereon. The second expandable portion is attached to the first expandable portion and is expandable upon expansion of the first expandable portion—i.e., the means used to expand the first expandable portion does not directly expand the second expandable portion.

The body of the present endovascular prosthesis has a generally longitudinal axis and is flexible. In a preferred embodiment, the second expandable portion is independently moveable between at least a first position and a second position with respect to the body, expanded or unexpanded. Thus, in the first position, the distal end and the proximal end of the body (including the first expandable portion) are aligned with the second expandable portion. In the second position, while securing the distal end and the proximal end of the body, the second expandable portion maintains a degree of independent movement. In this manner, the second expandable portion is "independently moveable" with respect to the body. In one embodiment, it is preferred that this independent movement is achieved by disposing the second expandable portion such that it may pivot with respect to the remainder of the endovascular prosthesis. It should be understood that, while the second expandable portion may be independently moveable with respect to the body, the final alignment of the distal end, the proximal end and second expandable portion (i.e., the alignment after blockage of the aneurysmal opening) is not particularly restricted and depends on factors such as the size and location of the aneurysm and the anatomy of the particular patient. The key point of this preferred embodiment is that the second expandable portion is capable of being independently moved with respect to the body.

The present endovascular prosthesis is believed to be particularly useful in the treatment of aneurysms such as those described hereinabove and is therefore believed to provide a significant alternative to the conventional surgical techniques described hereinabove. Additionally, it is envisaged that the present endovascular prosthesis may be used in the treatment of certain aneurysms which are diagnosed as being inoperable. The present endovascular prosthesis also is believed to provide a significant advantage of current endovascular approaches such as the Guglielmi Detachable Coil described hereinabove. Specifically, since the present endovascular prosthesis does not rely on insertion into the aneurysm of a metal packing material (e.g., platinum coil), the risk of rupturing the aneurysm is mitigated as is the risk of intra-aneurysmal rearrangement of the metal packing material and subsequent reappearance of the aneurysm.

BRIEF DESCRIPTION OF THE DRAWINGS

Embodiments of the present invention will be described with reference to the accompanying drawings, wherein like reference numerals denote like elements and in which.

DETAILED DESCRIPTION OF THE PREFERRED EMBODIMENTS

Figure 1:
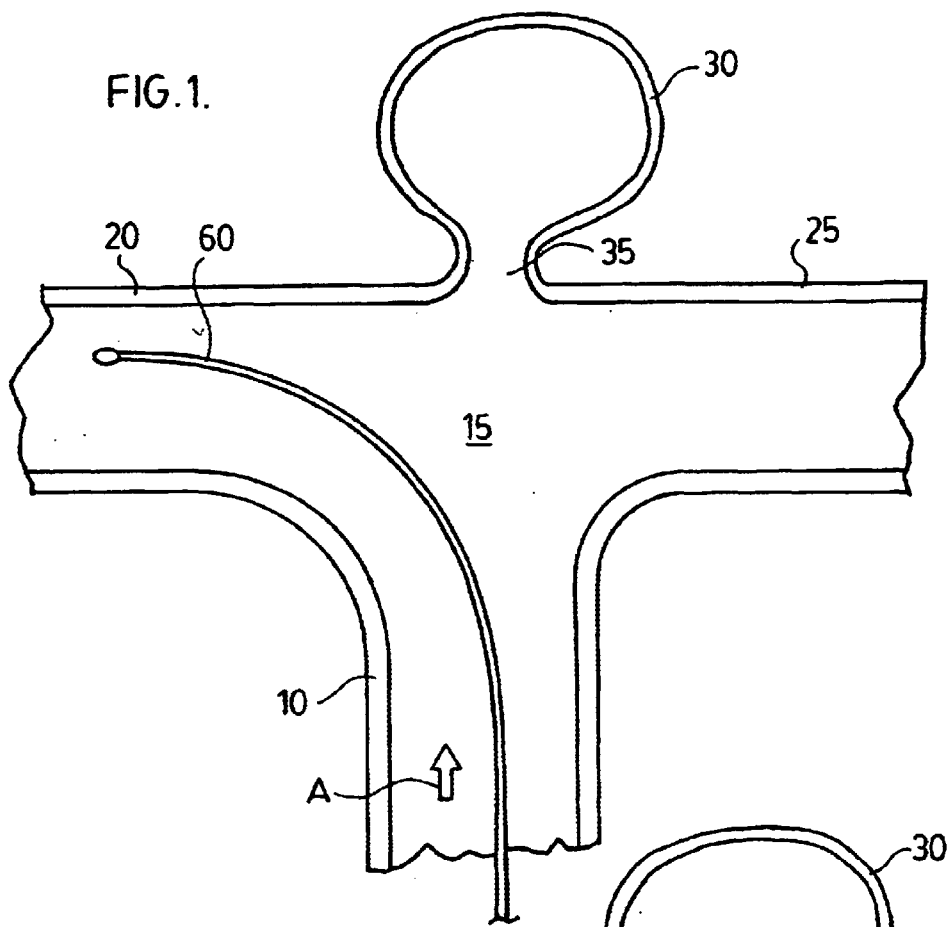
FIGS. 1–3 illustrate a cross-section of the terminal bifurcation of the basilar artery into which the present endovascular prosthesis is being delivered and implanted.

With reference to FIGS. 1–4, a first embodiment of the present endovascular prosthesis will be described with particular reference to implantation of same at the terminal bifurcation of the basilar artery.

Thus, there is illustrated a basilar artery 10 which terminates at a junction 15 which bifurcates into pair of secondary arteries 20, 25. Located at junction 15 is an aneurysm 30. Aneurysm 30 has an opening 35 (shown enlarged for illustrative purposes only) through which blood enters and sustains aneurysm 30.

An endovascular prosthesis 100 is mounted on a catheter 50.

Catheter 50 comprises an inflatable balloon 55 and a guidewire 60. Catheter 50, inflatable balloon 55 and guidewire 60 are conventional. As is known in the art, inflatable balloon 55 is moveable along guidewire 60.

Endovascular prosthesis 100 is constructed of a body 105. Body 105 comprises a proximal end 110 and a distal end 115. Endovascular prosthesis 100 further comprises an expandable leaf portion 120 (the second expandable portion) attached to a first expandable portion 130. As illustrated, leaf portion 120 comprises a covered portion 125. Endovascular prosthesis 100 further comprises a third expandable portion 135 connected to the first expandable portion 130 by a spine 140.

Body 105 is a generally tubular element and should be constructed to be sufficiently flexible such that it can be navigated to the target body passageway yet be sufficiently expandable such that it can be fixed at the proper location in target body passageway.

One approach to achieve this is to construct endovascular prosthesis 100 from a structure resembling a stent. As is known in the art, a stent is an expandable prosthesis which is generally used to obtain and maintain the patency of a body passageway (e.g., blood vessels, respiratory ducts, gastrointestinal ducts and the like). The two general design requirements of a stent are: (i) it must be sufficiently flexible in the unexpanded state such that it may be navigated to the target body passageway intact, and (ii) it must be sufficiently radially rigid in the expanded state to avoid the occurrence of restenosis and/or stent recoil. The most preferred embodiment of the present endovascular prosthesis is one for treating aneurysms and thus, is not a stent, per se, since design requirement (ii) need not be met—i.e., the aim of the present endovascular prosthesis is not to maintain patency of blocked body passageway. Rather, this preferred embodiment of the present endovascular prosthesis comprises one or more expandable elements for the purposes of securing the prosthesis in the correct position. Of course, the novel approach of dual expansion functionality of the present endovascular prothesis may be applied to stents in the appropriate application.

Thus, in this approach body 105 may be a porous tube having a porosity defined by a plurality of intersecting members (for clarity, the porosity of body 105 is not illustrated in FIGS. 1–4). The precise pattern of the intersecting members is not particularly restricted and should be chosen to achieve sufficient flexibility of the porous tube in the unexpanded state while having the potential to achieve at least some degree of expansion upon the application of radially outward forces on the tube. Typically, the plurality of intersecting members will be arranged to define a regular repeating pattern. See, for example, the various repeating patterns disclosed in the following copending patent applications:

Canadian patent application number 2,134,997 (filed Nov. 3, 1994);

Canadian patent application number 2,171,047 (filed Mar. 5, 1996);

Canadian patent application number 2,175,722 (filed May 3, 1996);

Canadian patent application number 2,185,740 (filed Sep. 17, 1996);

Canadian patent application number 2,192,520 (Dec. 10, 1996);

International patent application PCT/CA97/00151 (filed Mar. 5, 1997);

International patent application PCT/CA97/00152 (filed Mar. 5, 1997); and

International patent application PCT/CA97/00294 (filed May 2, 1997);

(hereinafter collectively referred to as the "Divysio patent applications") and the various references cited therein. While the repeating patterns disclosed in the Divysio patent applications are suited for use in stent designs, they may be modified to increase the flexibility of the tubular structure (e.g., by altering the polygonal design taught in the Divysio patent application applications) to be useful in a preferred embodiment of the present endovascular prosthesis notwithstanding that the resultant tubular structure may not be advantageously useful as a stent.

Body 105 may be constructed of any suitable material. In one preferred embodiment, body 105 is constructed of a plastically deformable material such as a metal, alloy or polymer. Non-limiting examples of suitable metals and alloys may be selected from the group comprising stainless steel, titanium, tantalum and the like. In this embodiment, the radially outward force used to expand body 105 may be applied by expansion of a catheter-mounted balloon, as will be discussed in more detail hereinbelow. In another preferred embodiment, body 105 is constructed of "shape memory" metal alloy (e.g., nitinol) capable of self-expansion at a temperature of at least about 30° C., preferably in the range of from about 30° to about 40° C. In this embodiment, it will be appreciated that an inherent radially outward force causes expansion of body 105 when it is exposed to an environment at the programmed self-expansion temperature. In yet another preferred embodiment, body 105 may be constructed of a biodegradable material. As is known in the art, a biodegradable material will degrade upon prolonged contact with body fluids and would be useful in the present endovascular prosthesis since aneurysm obliteration may occur within minutes after closing of the aneurysmal opening.

The manner by which body 105 is manufactured is not particularly restricted. Preferably, the body 105 is produced by laser cutting techniques applied to a tubular starting material. Thus, the starting material could be a thin-walled tube of a metal, alloy or polymer as described above which would then have sections thereof cut out to leave the desired repeating pattern discussed above. FIGS. 5–8 illustrate how the various elements of endovascular prosthesis 100 may be cut out of a tubular starting material (again, for clarity, the specific porosity of body 105 is not illustrated in FIGS. 5–8).

In an alternate embodiment, it is possible to construct body 105 having the desired porous repeating pattern from one or more pre-formed wires. In another alternate embodiment, it is possible to construct body 105 having the desired porous repeating pattern using a flat bed laser cutting technique, optionally combined with a welding technique.

Endovascular prosthesis 100 may further comprise a coating material thereon. The coating material may be disposed on the surface of the prosthesis. Further, the coating may be disposed on the interior and/or the exterior surface(s) of the prosthesis. The coating material can be one or more of a biologically inert material (e.g., to reduce the thrombogenicity of the prosthesis), a medicinal composition which leaches into the wall of the body passageway after implantation (e.g., to provide anticoagulant action, to deliver a pharmaceutical to the body passageway and the like), and the like.

Endovascular prosthesis 100 is preferably provided with a biocompatible coating in order to minimize adverse interaction with the walls of the body vessel and/or with the liquid, usually blood, flowing through the vessel. The coating is preferably a polymeric material, which is generally provided by applying to the prosthesis a solution or dispersion of preformed polymer in a solvent and removing the solvent. Non-polymeric coating material may alternatively be used. Suitable coating materials, for instance polymers, may be polytetraflouroethylene or silicone rubbers, or polyurethanes which are known to be biocompatible. Preferably, however, the polymer has zwitterionic pendant groups, generally ammonium phosphate ester groups, for instance phosphoryl choline groups or analogues thereof. Examples of suitable polymers are described in International Publication Number WO 93/16479. Polymers described in those specifications are hemo-compatible as well as generally biocompatible and, in addition, are lubricious. It is important to ensure that the surfaces of the prosthesis are completely coated in order to minimize unfavorable interactions, for instance with blood, which might lead to thrombosis in the parent vessel.

This good coating can be achieved by suitable selection of coating conditions, such as coating solution viscosity, coating technique and/or solvent removal step.

With further reference to FIG. 1, once it is desired to implant endovascular prosthesis 100, it is mounted on balloon 55 of catheter 50. Guidewire 60 is translated through basilar artery 10 in the direction of arrow A.

Figure 2:
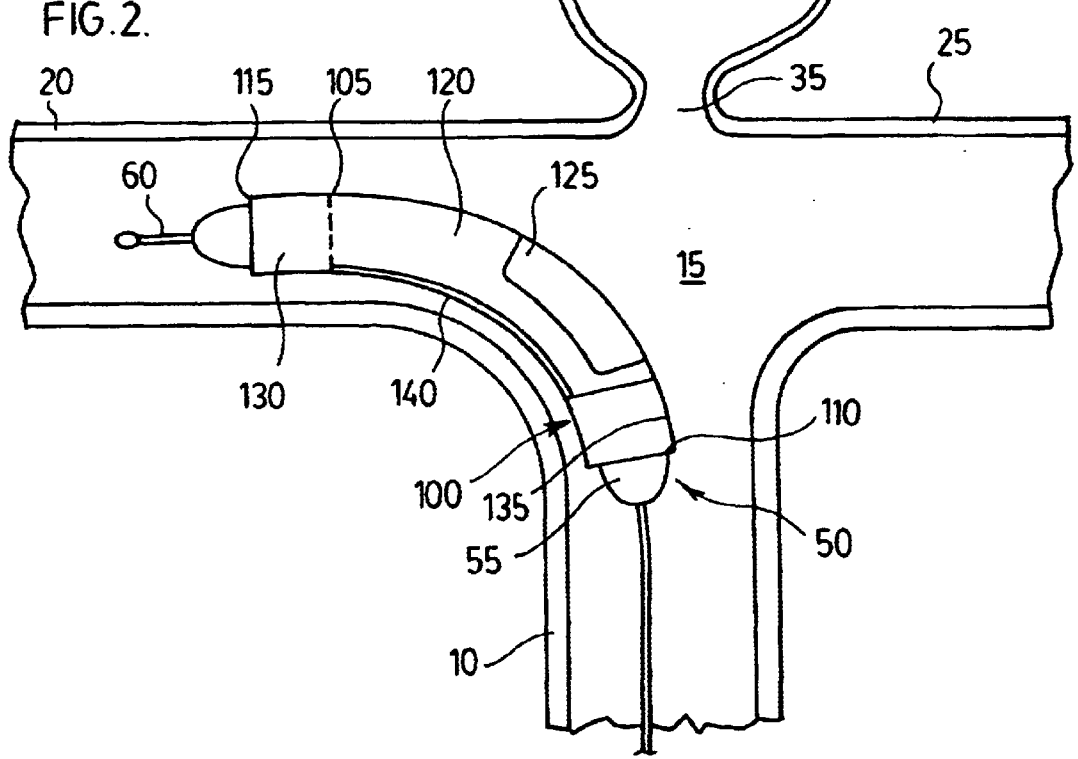

With reference to FIG. 2, endovascular prosthesis 100 mounted on balloon 55 of catheter 50 is navigated to the location of aneurysm 30 using conventional guidewire and fluoroscopy techniques. In the illustrated embodiment, distal end 115 of body 105 enters secondary artery 20. In practice, the secondary arteries at the bifurcation of the basilar artery are asymmetric and distal end 115 of body 105 is preferably navigated into the larger of the two secondary arteries. Further, in the illustrated embodiment, as body 105 is flexed on navigation into secondary artery 20, leaf portion 120 lifts or moves out of alignment with respect to the tubular plane of body 105 to define an opening 135.

Figure 3:
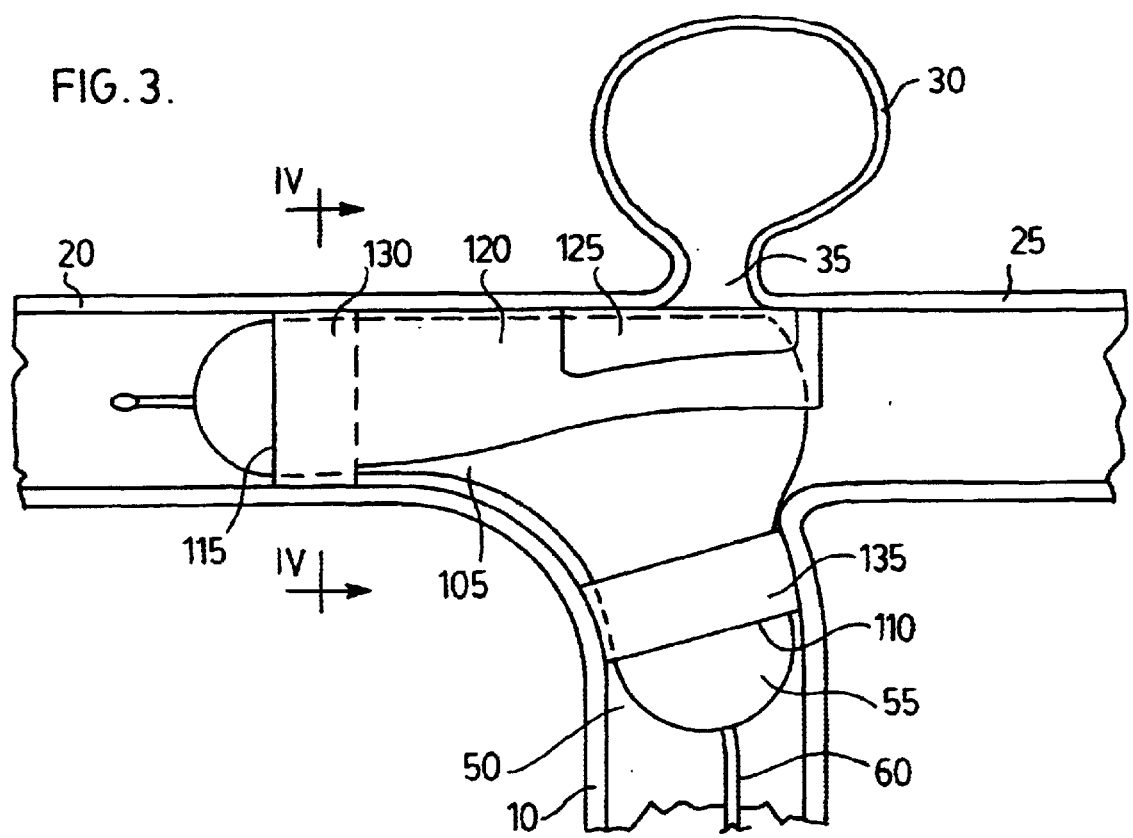
Figure 4:
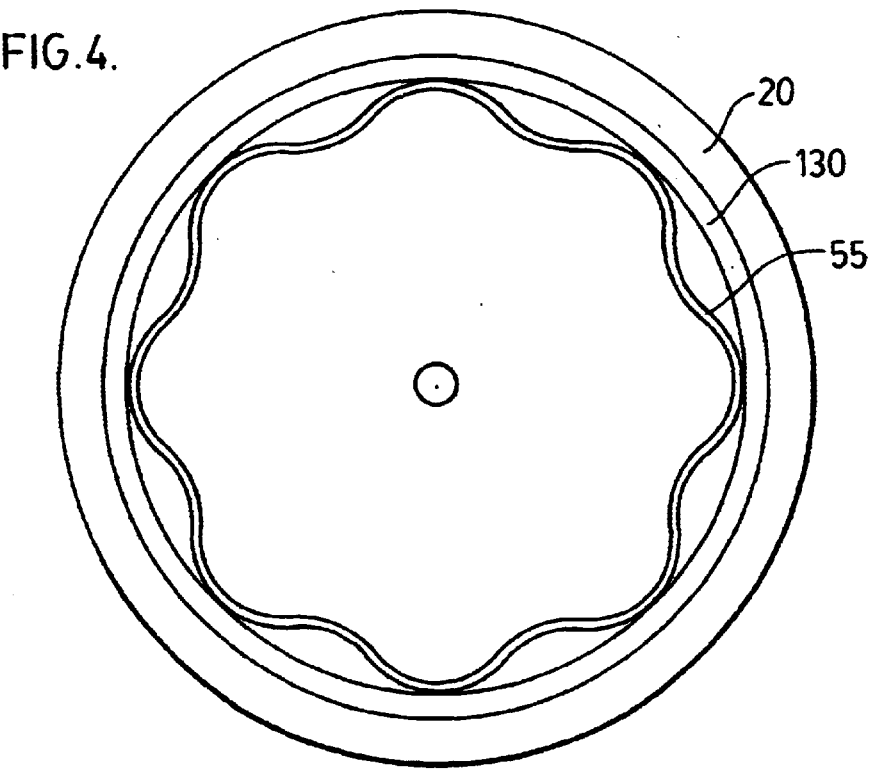
FIG. 4 is an enlarged sectional view taken along line IV—IV in FIG. 3.
Figures 5, 6:
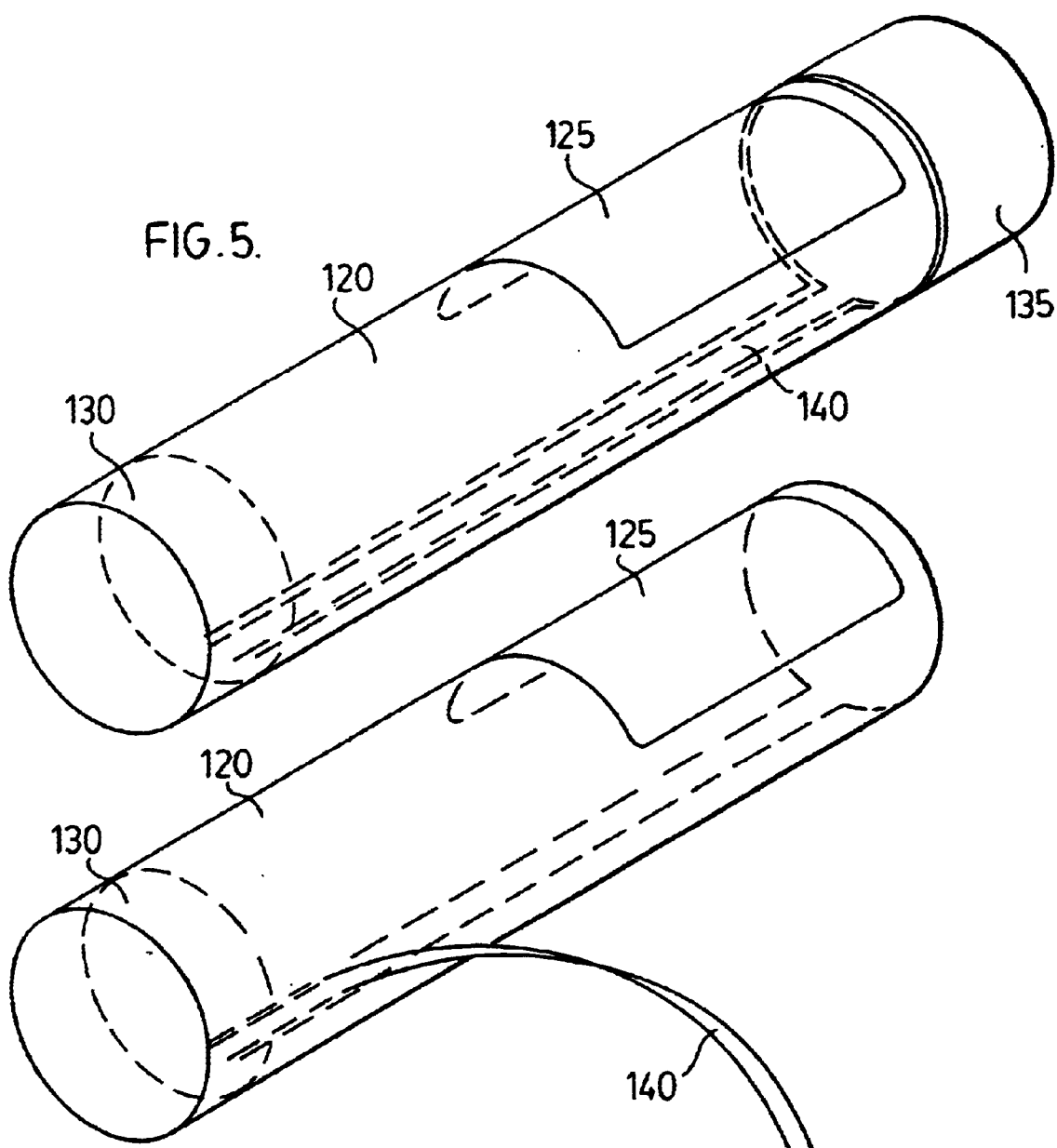
FIGS. 5–8 illustrate a perspective view of a preferred embodiment of the present endovascular prosthesis shown in schematic.
Figure 7:
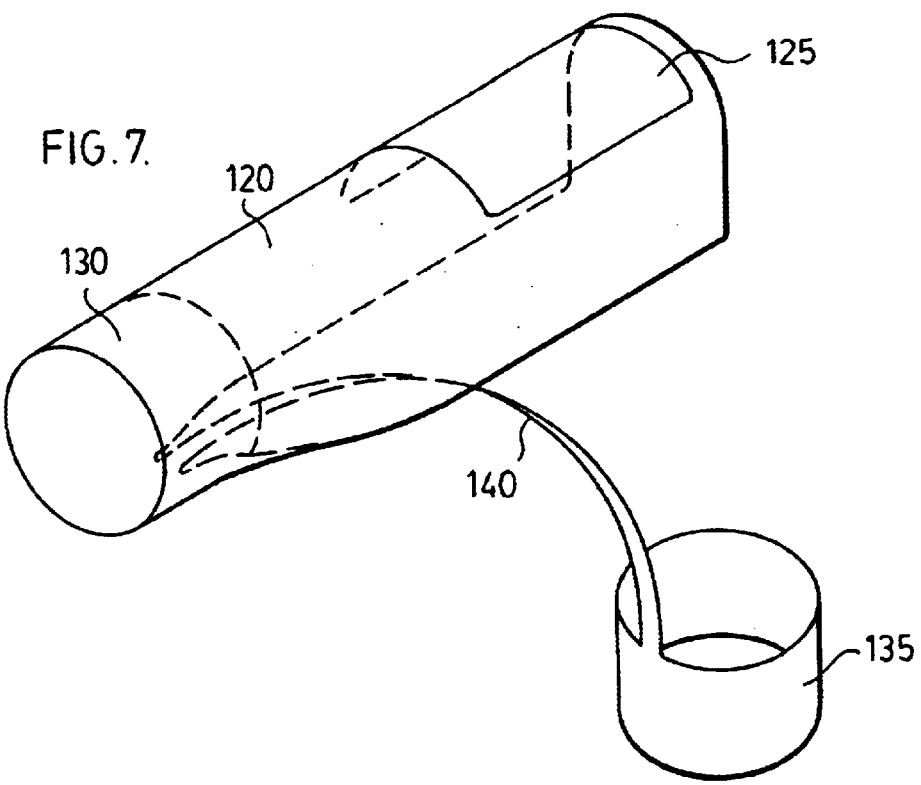
Figure 8:
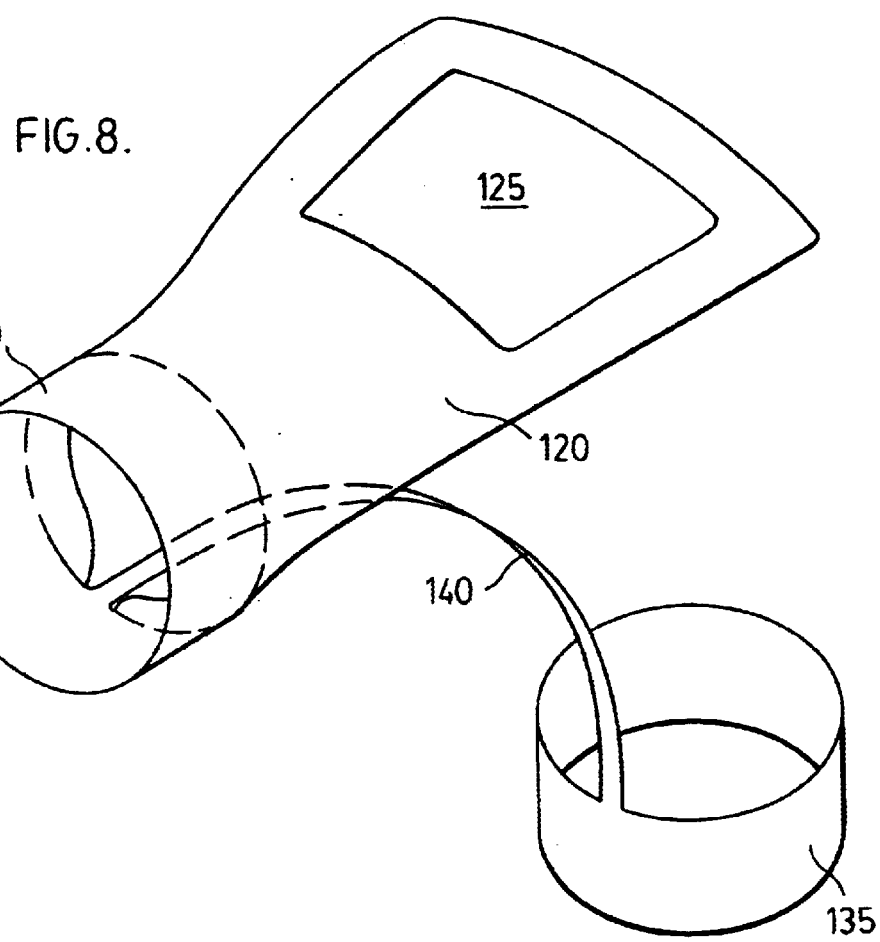

With reference to FIGS. 3 and 4, once endovascular prosthesis 100 is in the correct position, balloon 55 is expanded thereby exerting radially outward forces on first expandable portion 130 and third expandable portion 135. Initially, this results in expansion of body 105 such that a portion of it is urged against the walls of both of basilar artery 10 and secondary artery 20. This results in expansion of leaf portion 120 as will be described in further detail hereinbelow. In the embodiment illustrated in FIG. 3, balloon 55 is expanded to a degree whereby leaf portion 120 expands and is urged against the walls of secondary arteries 20, 25 in a manner which results in blocking of opening 35 of aneurysm 30.

With reference to FIG. 4, balloon 55 is deflated and, together with guidewire 60, withdrawn from endovascular prosthesis 100. In the illustrated embodiment, endovascular prosthesis 100 is secured in position by first expandable portion 130 and third expandable portion 135 being urged against the walls of basilar artery 10 and secondary artery 20. Further, in the illustrated embodiment, leaf portion 120 is secured in position by a combination of forces against it by the flow of the blood and the inherent forces upon flexure of body 105 to navigate distal end 115 into secondary artery 20. Once leaf portion 120 blocks opening 35, aneurysm 30 is obliterated thereafter.

Figure 9:
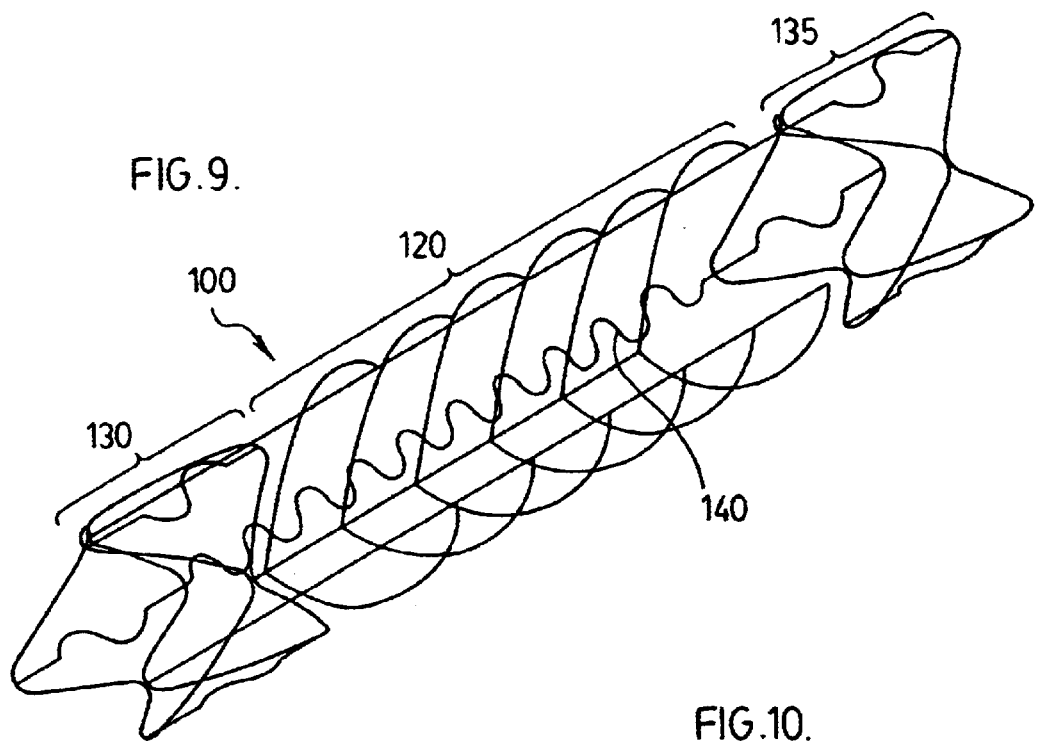
FIG. 9 illustrates a perspective view of a particularly preferred embodiment of the L present endovascular prosthesis.
Figure 10:
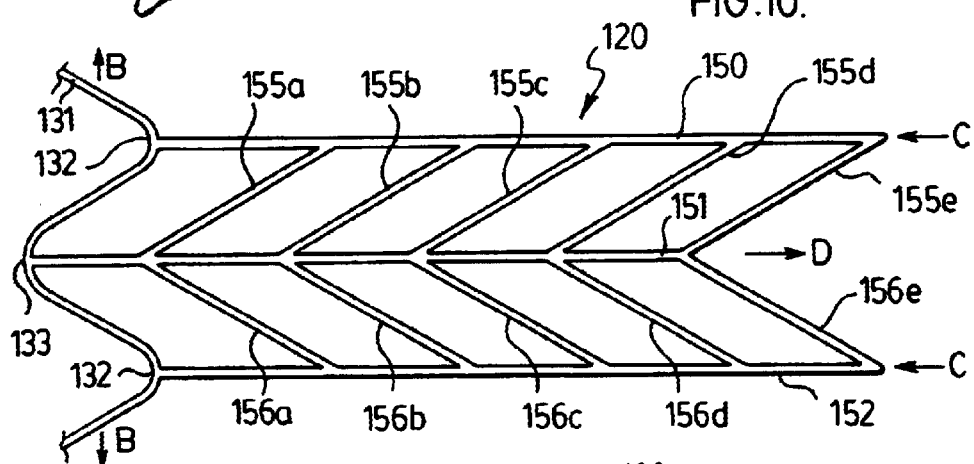
FIGS. 10–11 illustrate a two-dimensional representation of one embodiment of the "chevron" effect exhibited in the present endovascular prosthesis.
Figure 11:
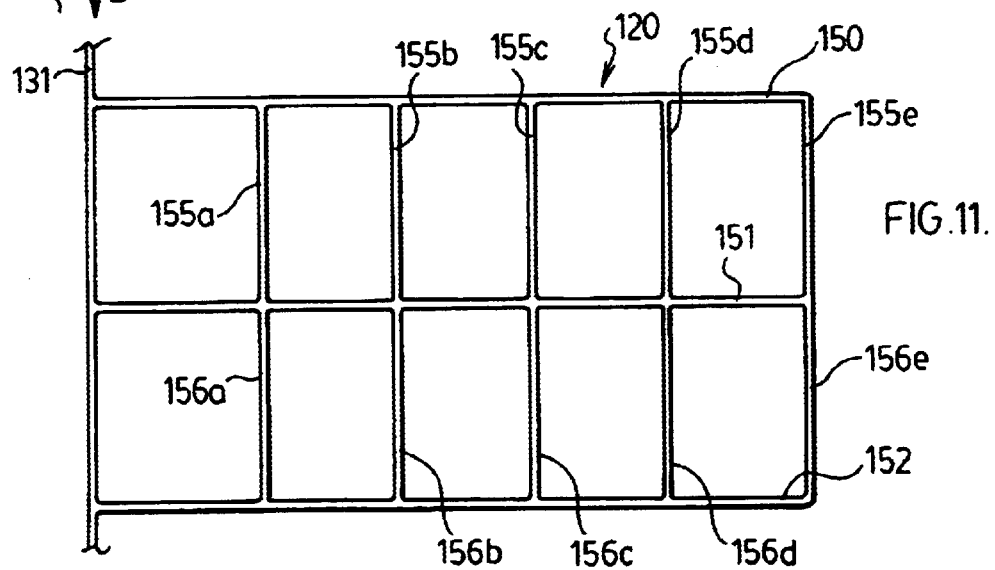

With reference to FIGS. 9–11, there is illustrated a particularly preferred embodiment of present endovascular prosthesis 100. Endovascular prosthesis 100, as illustrated, is produced by etching the illustrated design from a thin-walled tube constructed of a plastically deformable material (e.g., stainless steel). As shown a single spine 140 is all that interconnects first expandable region 130 and third expandable region 135.

With reference to FIGS. 10–11, the "chevron" function of leaf portion 120 (the second expandable region) is illustrated. Thus, leaf portion 120 comprises a series of longitudinals 150, 151, 152 which are substantially parallel to one another. Longitudinals 150, 151, 152 are interconnected by pairs of struts 155a/156a, 155b/156b, 155c/156c, 155d/156d and 155e/156e. As will be apparent, struts 155/156 meet at an intersection point (at longitudinal 151) to define an acute angle.

Longitudinals 150, 151, 152 are connected to a circumferential strut 131 comprised in first expandable portion 130. As shown, in two dimensions, strut 131 has a sinusoidal (or wave-like or undulating or meandering) design. As will be apparent to those of skill in the art, the sinusoidal design of strut 131 defines, in two dimensions, a convex apex 132 and a concave apex 133. As used throughout this specification, the term "concave apex" is intended to mean an apex which is directed into first expandable portion 130 and term "convex apex" is intended to mean an apex which is directed away from first expandable portion 130. In the illustrated embodiment, strut 131 comprises a plurality of alternating convex apices 132 and concave apices 133. As shown, longitudinals 150 and 152 are connected to convex apices 132, and longitudinal 151 is connected to concave apex 133.

When first expandable portion 130 is expanded as described hereinabove, this results in radial expansion of circumferential strut 131. Thus, as first expandable portion 130 expands circumferential strut 131 is stretched in the direction of arrows B resulting in substantial straightening of strut 131. Straightening of strut 131 results in movement of longitudinals 150 and 152 in the direction of arrows C (i.e., pulling in toward strut 131) and in movement of longitudinal 151 in the direction of arrow D (i.e., pushing away from strut 131). At the same time, the acute angle formed between struts 155/156 opens up such, in the optimum case (FIG. 11), struts 155/156 are collinear.

As will be apparent to those of skill in the art, the surface area of expanded leaf portion 120 (FIG. 11) is greater than that of unexpanded leaf portion 120 (FIG. 10). Thus, it can be appreciated that the present endovascular prothesis, having a given tubular dimension, has a leaf portion which, upon expansion, will have a surface area greater than the surface area of a leaf portion having the same tubular dimension but which simply opens (i.e., it uncurls but does not expand, per se) during deployment.

For clarity, the description above with reference to FIGS. 9–11 does not include covered portion 125. In practice, it is preferred that most or all of leaf portion 120 is covered with a material suitable to: (i) withstand expansion of leaf portion 120, and (ii) block the opening 35 of aneurysm 30 after deployment. The nature of the material used for this purpose is not particularly restricted. Preferably, the material comprises Cardiothane 51™ (Kontron Instruments, Inc., Everett, Mass.), a medical grade polyurethane/silcone polymer which is known to be useful in intravascular devices (e.g., as a balloon material for intra-aortic cardiac assist devices). Thus, a "bare" leaf portion 120 may be initially coated with a 5.7% weight:volume (w:v) solution of Cardiothane 51™ dissolved in an organic solvent (e.g., 2:1 tetrahydrofuran: 1,4-dioxane). The initially coated leaf portion 120 may then be further covered with an 11.7% w:v solution of Cardiothane 51™ dissolved in the same solvent. When the polymer is dry, the struts of leaf portion 120 are substantially embedded within the polyurethane-silicone cover. The covered leaf portion 120 may then be sterilized with ethylene-oxide. For more information about this approach, see "In Vivo Evaluation of Porous Versus Skinned Polyurethane-Polydimethylsiloxane Small Diameter Vascular Grafts" by Okoshi et al., *ASAIO Transactions* 1991; 37: M480–M481.

Figure 12:
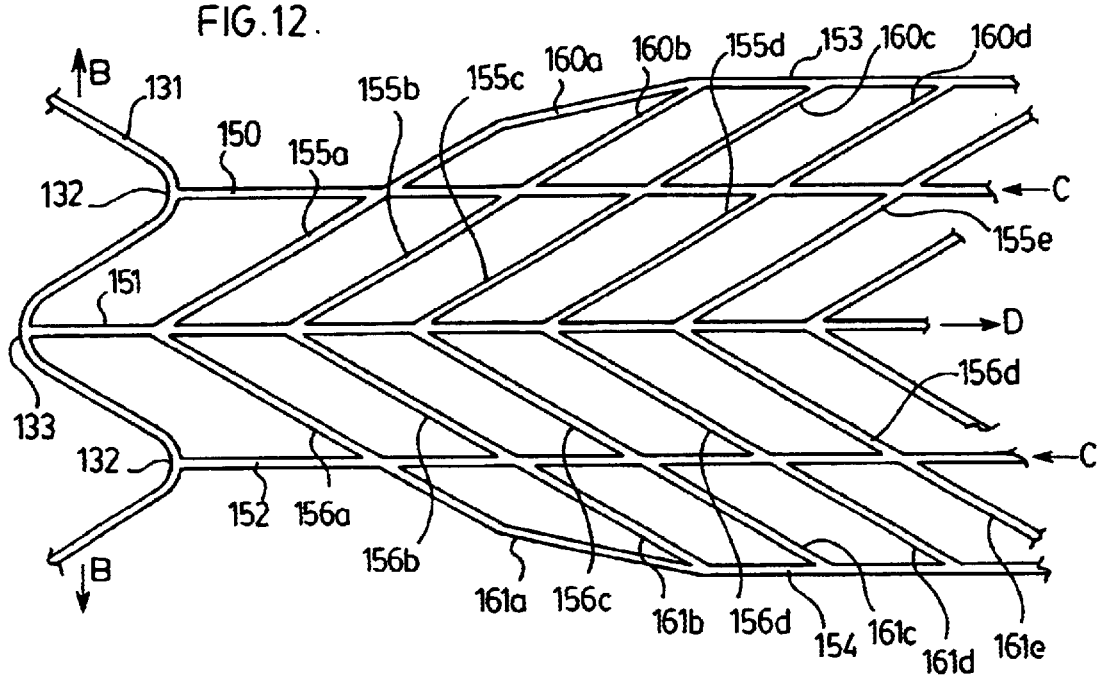
FIGS. 12–13 illustrate a two-dimensional representation of another embodiment of the "chevron" effect exhibited in the present endovascular prosthesis.
Figure 13:
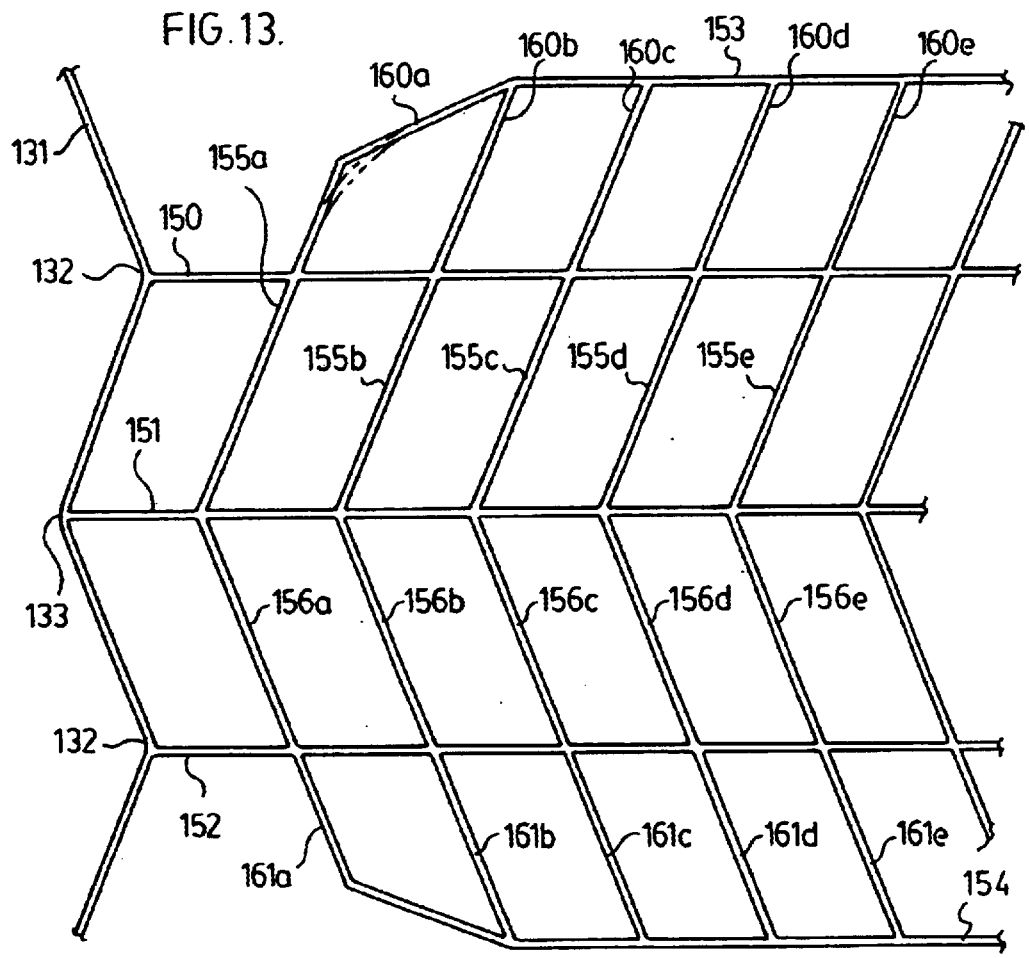

In FIGS. 12 and 13 there is illustrated a variation to leaf portion 120 illustrated in FIGS. 10 and 11 (Note: like reference numerals in FIGS. 10–13 are intended to denote like elements and vice versa). Thus, as illustrated, the variation in FIGS. 12 and 13 comprises an extra pair of longitudinals 153, 154. Longitudinals 150 and 153 are interconnected by a plurality of struts 160a, 160b, 160c, 160d, 160e, etc. Similarly, longitudinals 152 and 154 are interconnected by a plurality of struts 161a, 161b, 161c, 161d, 161e, etc. As shown longitudinals 153, 154 are not directly connected to circumferential strut 131. This facilitates independent movement of leaf portion 120 with respect to first expandable portion 130 as discussed hereinabove while optimizing the surface area of leaf portion 120 in the expanded state (FIG. 13). Further, it can be seen that struts 160a, 161a are bent (or angled) in the unexpanded state of leaf portion 120 (FIG. 12). This facilitates expansion of leaf portion 120 as shown in FIG. 13.

Figure 14:
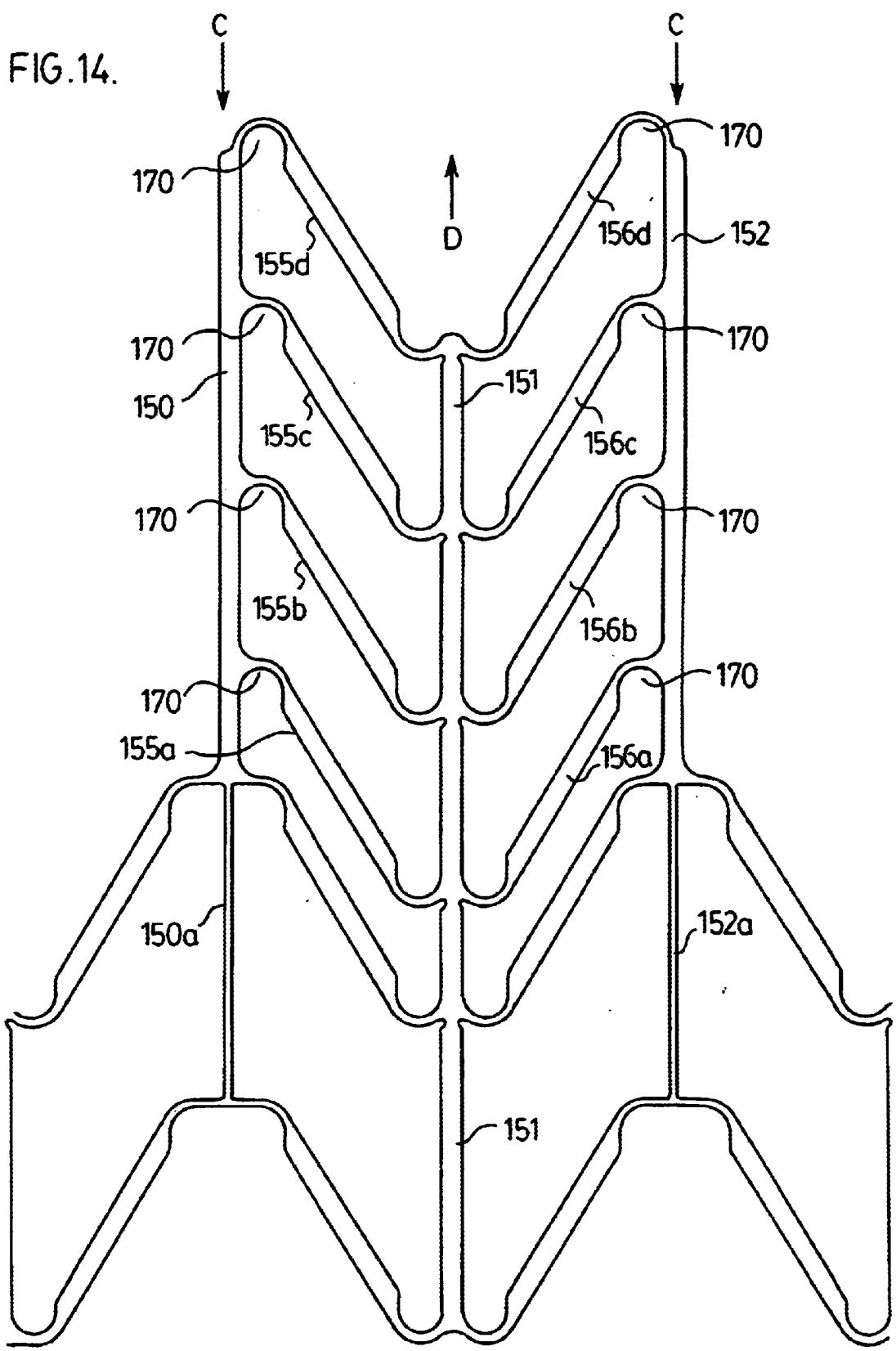
FIG. 14 illustrates a first embodiment of an expandable leaf portion useful in the present endovascular prosthesis.

In FIG. 14, there is illustrated a variation to leaf portion 120 illustrated in FIGS. 10 and 11 (Note: like reference numerals in FIGS. 10, 11 and 14 are intended to denote like elements and vice versa). One variation in the leaf portion illustrated in FIG. 14 is the provision of longitudinal struts 150a and 152a which are thinner than longitudinals 150 and 152, respectively, and longitudinal 151. This variation serves to substantially equalize the stress developed in struts 150a and 152a in the direction of arrow C with the force applied to longitudinal 151 in the direction of arrow D. Further, a series of connections 170 between longitudinals 150, 151, 152 and struts 155(a,b,c,d) and 156(a,b,c,d) have been modified to be thinner and of a larger internal radius. This variation serves to facilitate bending of connections 170 and opening or expansion of the leaf portion.

Figure 15:
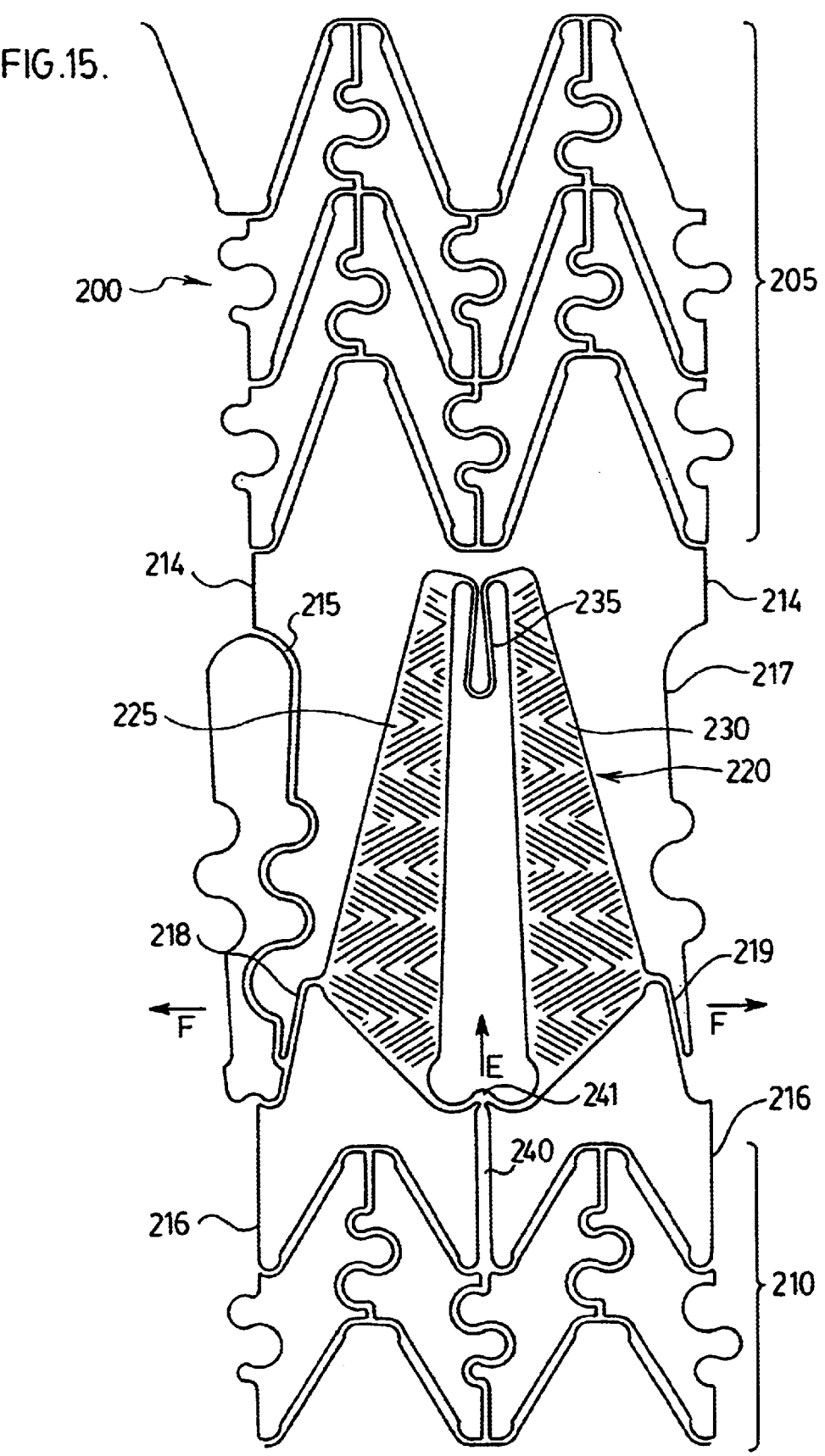
FIG. 15 illustrates a second embodiment of an expandable leaf portion useful in the present endovascular prosthesis.

With reference to FIG. 15, there is illustrated a variation to the leaf portion illustrated in FIGS. 10–14.

As shown, FIG. 15 illustrates a two dimensional representation of a preferred embodiment of the present endovascular prosthesis 200. Prosthesis 200 comprises a first expandable portion 205 and a second expandable portion 210. First expandable portion 205 and second expandable portion 210 are interconnected by struts 214, 216 and spines 215, 217.

In the illustrated embodiment, first expandable portion 205 and second expandable portion 210 each have a porous surface defined by a series of interconnected members which form a pattern similar to the patterns disclosed in the Divysio patent application referred to hereinabove.

Endovascular prosthesis 200 comprises a leaf portion 220. Leaf portion 220 comprises a pair of jaw members 225,230. Jaw members 225,230 each comprise a surface which has microcuts disposed therein. Such microcuts may be disposed in jaw members 225,230 by a conventional laser cutting technique or the like.

Jaw members 225,230 are interconnected to one another at one end thereof by a connection member 235. Further, jaw member 225 is connected to spine 215 via a strut 218. Similarly, jaw member 230 is connected to spine 217 via a strut 219. As illustrated, strut 218 also serves to interconnect jaw member 225 and strut 216. Similarly, strut 219 also serves to interconnect jaw member 230 and strut 216.

When second expandable portion 210 is expanded as described hereinabove, a connection strut 240 interconnecting a junction 241 between jaw members 225,230 and second expandable portion 210 results in movement of connecting strut 240 in the direction of arrow E (i.e., pushing junction 241 toward connecting member 235). Concurrently, struts 218,219 pull on jaw members 225,230 in the direction of arrows F such that jaw members 225,230 pivot about junction 241 with the result that connection member 235 unfolds or opens up.

Attached to jaw members 225,230 is a cover material (not shown for clarity) which, upon expansion of jaw members 225,230 unfolds to optimize the surface area of leaf portion 220.

The nature of the coating material is not particularly restricted provided it is biomedical in nature (i.e., it can be safely delivered to and retained in a lumen) and may be of the type of coating material in connection with the embodiments described hereinabove. The coating material may be stretchable (as described hereinabove) or non-stretchable. The coating material may be Dacron™, Goretex™ and the like. The coating material may be stitched to jaw members 225,230. Alternatively, the coating material maybe adhered to jaw members 225,230. The particular method of securing the coating layer to jaw members 225,230 is not particularly restricted.

The coating material may be applied to jaw members 225,230 prior to expansion of leaf portion 220. Alternatively, it is possible to partially or fully pre-expand leaf portion 220, apply the coating material and thereafter crimp or otherwise return leaf portion 220 to a suitable predeployment state.

The preferred embodiment of endovascular prosthesis 200 illustrated in FIG. 15 is particularly advantageous since it allows expansion of leaf portion 220 without the requirement that a force necessary to stretch a coating material be applied (contrast this with the embodiments illustrated in FIGS. 9–14).

Further, the provision of spines 215,217 in endovascular prosthesis 200 serve the additional benefit of conferring "preferential flexibility" to expandable prosthesis 200. This preferential flexibility tends to maintain leaf portion 220 on the outside of an arc described by the flexed prosthesis and helps urge leaf portion 220 into position against the neck of the aneurysm.

In the illustrated embodiment of FIG. 15, leaf portion 220 is expanded by the concurrent "pushing" action of connecting strut 240 and "pulling" actions of struts 218,219 described above. Those of skill in the art will of course appreciate that, in some cases, it may be possible to modify the illustrated embodiment to achieve expansion of leaf portion 220 with either "pushing" or "pulling" as described, or even by some other action.

In this and the foregoing illustrated embodiments of the present endovascular prosthesis, it is possible, and even preferred in some cases, to use tabs or similar devices on the edge of the leaf portion to obviate lifting of the leaf from the catheter or other delivery system used to deliver the prosthesis. Such tabs may increase the circumferential wrap around the balloon allowing the leaf portion to maintain a low profile along the length of the balloon during delivery of the device. These tabs may be simply designed to "break away" or otherwise release the leaf portion from the balloon (e.g., during deployment of the prosthesis) to achieve the benefits described above.

Other variations and modifications of the specific embodiments described hereinabove which do not depart from the scope and spirit of the invention will be immediately apparent to those of skill in the art having this specification in hand. For example, while in various of the illustrated embodiments, the leaf portion is shown pointing toward the proximal end of the prosthesis during delivery, this is not essential and, in some cases, a reverse orientation may be preferred. Further, while in various of the illustrated embodiments, an endovascular prosthesis to treat a brain aneurysms is shown, it will be apparent to those of skill in the art that the present endovascular prosthesis may be advantageously used to treat other types of aneurysms and used in other (non-aneurysm) endovascular applications. Still further, while in various of the illustrated embodiments, a pair of expandable, annular rings is shown, it is possible to construct the prothesis using a single expandable annular ring or 3 or more expandable annular rings. Still further, while in various of the illustrated embodiments, the expansible portion of the body comprises a pair of rings having a porous structure, it is possible to use rings having a non-porous structure, for example, by folding down the rings and maintaining them in this state using a removable mechanical restraint which, when removed, allows the rings to unfold into a deployed state (in this embodiment, the rings would be dimensioned to their final implanted diameter and then folded down—see for example, International Publication Number WO 95/26695). Other modifications which do not deviated from the spirit and scope of the invention will be immediately apparent to those of skill in the art having the present specification in hand.

All publications, patents and patent applications referred to herein are incorporated by reference in their entirety to the same extent as if each individual publication, patent or patent application was specifically and individually indicated to be incorporated by reference in its entirety.

What is claimed is:

1. An expandable endovascular prosthesis comprising:
    a body having a proximal end and a distal end;
    a first expandable portion disposed between the proximal end and the distal end, the first expandable portion being (i) made from a plastically deformable material, and (ii) expandable from a first, unexpanded state to a second, expanded state with a radially outward force to cause plastic deformation thereof to urge the first expandable portion against a vascular lumen; and
    a second expandable portion attached to the first expandable portion, the second expandable portion being made from a plastically deformable material;
    expansion of the first expandable portion causing plastic deformation thereof which causes expansion and plastic deformation of a free end of the second expandable portion so, that the second expandable portion is larger after expansion.

2. The prosthesis defined in claim 1, wherein the second expandable portion comprises a porous surface.

3. The prosthesis defined in claim 2, wherein the second expandable portion comprises a covering layer which covers at least a portion of the porous surface.

4. The prosthesis defined in claim 3, wherein the covering layer comprise an elastic material capable of stretching upon expansion of the second expandable portion.

5. The prosthesis defined in claim 2, wherein the porous surface is defined by a plurality of interconnected struts.

6. The prosthesis defined in claim 5, wherein the plurality of interconnected struts comprises a plurality of first longitudinals.

7. The prosthesis defined in claim 6, wherein the plurality of first longitudinals are connected to one another by a plurality of second struts disposed at an acute angle with respect to the first longitudinals.

8. The prosthesis defined in claim 6, wherein at least some of the longitudinals are connected to a first edge of the first expandable portion.

9. The prosthesis defined in claim 8, wherein the first edge comprises a circumferentially meandering pattern.

10. The prosthesis defied in claim 9, wherein the circumferentially meandering pattern comprises a plurality of apices.

11. The prosthesis defined in claim 10, wherein the plurality of apices comprise a first set of convex apices and a second set of concave apices.

12. The prosthesis defined in claim 11, wherein the convex apices and concave apices alternate with respect to one another.

13. The prosthesis defined in claim 11, wherein at least two longitudinals are connected to an adjacent pair comprising a convex apex and concave apex.

14. The prosthesis defined in claim 5, wherein the plurality of interconnected struts further comprises a plurality of second longitudinals which are unconnected to the first expandable portion.

15. The prosthesis defined in claim 1, wherein the first expandable portion is tubular.

16. The prosthesis defined in claim 1, wherein the second expandable portion is independently moveable with respect to the first expandable portion.

17. The prosthesis defined in claim 1, wherein the second expandable portion is porous.

18. The prosthesis defined in claim 1, wherein the body comprises a third expandable portion connected to the first expandable portion which is expandable from a first, unexpanded state to a second, expanded state with a radially outward force thereon.

19. The prosthesis defined in claim 18, wherein the first expandable portion and the third expandable portion are connected to one another by at least one strut.

20. The prosthesis defined in claim 1, wherein the first expandable portion comprises a porous surface.

21. The prosthesis defined in claim 18, wherein the third expandable portion comprises a porous surface.

22. The prosthesis defined in claim 18, wherein the first expandable portion and the third expandable portion each comprise a porous surface.

23. The prosthesis defined in claim 1, wherein the first expandable portion and the second expandable portion a integrally formed.

24. The prosthesis defined in claim 18, wherein the first expandable portion, second expandable portion and third expandable portion are integrally formed.

25. The prosthesis defined in claim 1, wherein the body comprises a substantially tubular shape.

26. The prosthesis defined in claim 1, wherein the body comprises a substantially porous surface.

27. The prosthesis defined in claim 1, wherein the body is constructed from a plastically deformable material.

28. The prosthesis defined in claim 1, wherein the body is constructed from a self-expanding material.

29. The prosthesis defined in claim 1, wherein the body is constructed from a biodegradable material.

* * * * *